United States Patent
Sarvestani et al.

(10) Patent No.: US 9,387,008 B2
(45) Date of Patent: Jul. 12, 2016

(54) AXIAL SURGICAL TRAJECTORY GUIDE, AND METHOD OF GUIDING A MEDICAL DEVICE

(75) Inventors: Amir Sarvestani, Freiburg (DE); Hans Schoepp, Freiburg (DE); Klaus Welte, Freiburg (DE)

(73) Assignee: STRYKER EUROPEAN HOLDINGS I, LLC, Kalamazoo, MI (US)

( * ) Notice: Subject to any disclaimer, the term of this patent is extended or adjusted under 35 U.S.C. 154(b) by 385 days.

(21) Appl. No.: 13/228,083

(22) Filed: Sep. 8, 2011

(65) Prior Publication Data

US 2013/0066192 A1    Mar. 14, 2013

(51) Int. Cl.
| | |
|---|---|
| A61B 5/05 | (2006.01) |
| A61B 17/34 | (2006.01) |
| A61B 19/00 | (2006.01) |
| A61B 17/00 | (2006.01) |

(52) U.S. Cl.
CPC ............... *A61B 17/3403* (2013.01); *A61B 5/05* (2013.01); *A61B 19/201* (2013.01); *A61B 2017/00221* (2013.01); *A61B 2017/3407* (2013.01)

(58) Field of Classification Search
CPC ................................ A61B 5/05; A61B 19/201
USPC .................................................. 600/407–480
See application file for complete search history.

(56) References Cited

U.S. PATENT DOCUMENTS

| | | | |
|---|---|---|---|
| 4,583,538 A | 4/1986 | Onik et al. | |
| 4,733,661 A | 3/1988 | Palestrant | |
| 4,930,525 A | 6/1990 | Palestrant | |
| 5,053,042 A | 10/1991 | Bidwell | |
| 5,102,391 A | 4/1992 | Palestrant | |
| 5,280,427 A | 1/1994 | Magnusson et al. | |
| 5,868,757 A | 2/1999 | Koutrouvelis | |
| 6,122,538 A * | 9/2000 | Sliwa et al. | ............ 600/407 |
| 6,159,221 A | 12/2000 | Chakeres | |
| 6,695,786 B2 | 2/2004 | Wang et al. | |

(Continued)

FOREIGN PATENT DOCUMENTS

| | | |
|---|---|---|
| DE | 202009013604 U1 | 2/2010 |
| EP | 0 414 130 | 8/1990 |

(Continued)

OTHER PUBLICATIONS http://www.activiews.com/us-technology/, "Technology", Printed Jun. 13, 2011, 2 pages.

(Continued)

*Primary Examiner* — Vani Gupta
(74) *Attorney, Agent, or Firm* — Howard & Howard Attorneys PLLC

(57) ABSTRACT

A surgical trajectory guide to guide a medical device to a pivot point has a base that can be attached to a patient, an axial guide member connected with the base and aligned with a pivot point along a first axis in fixed relation to the base and a second axis perpendicular to the first axis. The guide member has a longitudinal axis, and is connected to the base such that the longitudinal axis always passes through the pivot point, and the axial guide member is prevented from rotating around the longitudinal axis. The guide further has at least one electronic angle sensor that can automatically sense a first angle of the axial guide member relative to the local gravity vector about the first axis and a second angle of the axial guide member relative to the local gravity vector about the second axis without having to level the base.

20 Claims, 8 Drawing Sheets

(56) References Cited

U.S. PATENT DOCUMENTS

| | | | |
|---|---|---|---|
| 6,872,213 | B2 | 3/2005 | Chakeres |
| 6,921,406 | B1 | 7/2005 | Chakeres |
| 7,277,594 | B2 | 10/2007 | Hofstetter et al. |
| 7,824,417 | B2 | 11/2010 | Magnusson et al. |
| 7,876,942 | B2 | 1/2011 | Gilboa |
| 7,909,815 | B2 | 3/2011 | Whitmore, III et al. |
| 7,925,328 | B2 | 4/2011 | Urquhart et al. |
| 8,290,570 | B2 | 10/2012 | Hoppe et al. |
| 2004/0034330 | A1* | 2/2004 | Bierman et al. ............... 604/500 |
| 2004/0073279 | A1* | 4/2004 | Malackowski et al. ......... 607/88 |
| 2005/0033315 | A1 | 2/2005 | Hankins |
| 2005/0116673 | A1 | 6/2005 | Carl et al. |
| 2006/0064010 | A1 | 3/2006 | Cannon, Jr. et al. |
| 2007/0078328 | A1 | 4/2007 | Ozaki et al. |
| 2008/0183191 | A1* | 7/2008 | Schoepp ....................... 606/130 |
| 2008/0200798 | A1 | 8/2008 | Eklund et al. |
| 2010/0016865 | A1 | 1/2010 | Kieper et al. |
| 2010/0030061 | A1 | 2/2010 | Canfield et al. |
| 2010/0036384 | A1 | 2/2010 | Gorek et al. |
| 2010/0249657 | A1 | 9/2010 | Nycz et al. |

FOREIGN PATENT DOCUMENTS

| | | |
|---|---|---|
| EP | 0 535 378 | 10/1991 |
| EP | 1 977 704 | 1/2007 |
| WO | WO 2010102197 A2 | 9/2010 |
| WO | WO 2011082517 A1 | 7/2011 |

OTHER PUBLICATIONS http://www.healthcare.philips.com/us_en/products/ultrasound/systems/percunav/percunav.wpd, "PercuNav Image Fusion and Navigation", Printed Jun. 13, 2011, 2 pages.

http://www.wikiradiography.com/page/Gantry, "Gantry", Printed Jul. 20, 2011, 3 pages.

http://www.memsnet.org/mems/what_is.html., "What is MEMS Technology?", Printed Jul. 18, 2011, 3 pages.

http://www.apariomed.com/seestar.html., "SeeStar", Printed Jun. 15, 2011, 1 page; and Product sheet, 2 pages.

http://www.ascension-tech.com/docs/2010/GE_03-25.pdf, Press Release, "Mar. 25, 2010: GE Healthcare Using Ascension Sensors to Guide Biopsy Needles to Internal Targets", 2 pages.

http://www.civco.com/new/ultraproe/, Press Release, "CIVCO's eTRAX™ and Ultra-Pro e™ Offer Clinicians Needle Tracking plus New Generation Guidance", Printed Jun. 9, 2011, 1 page. Article is currently located at Webpage: http://www.mermaidmedical.dk/news_p.html.

English language translation for DE 202009013604 extracted from epacenet.com database Aug. 27, 2013, 8 pages.

English language translation for WO 2011082517 extracted from espacenet.com database Aug. 27, 2013, 18 pages.

European Search Report for Application No. 12006070.2-1269 dated Dec. 13, 2012, 5 pages.

\* cited by examiner

AXIAL SURGICAL TRAJECTORY GUIDE, AND METHOD OF GUIDING A MEDICAL DEVICE

BACKGROUND OF THE INVENTION

1. Field of the Invention

The present invention relates to apparatus, and methods related to guiding an axial medical instrument, such as a needle or probe, during a medical procedure.

2. Description of the Background of the Invention

During medical procedures it is often necessary for a surgeon to insert an axial surgical instrument, such as a needle, shunt, or probe, into a patient to reach a pre-selected target within the body of the patient. Some exemplary surgical procedures where this necessary include biopsy procedures and invasive neurosurgical procedures. In order to obtain relatively accurate placement of the axial surgical instrument, it is currently customary to use navigation techniques that rely on one or more images of the patient that include the target, such as well known computed tomography (CT) techniques, which provide three-dimensional volume image information of the patients body (i.e., a "CT image" or "CT data set"). As used herein, the term CT is not limited to a particular scanning technology, and encompasses any available technology, such as X-ray, 2D projection X-ray, C arm devices, magnetic resonance imaging, ultrasound, and other types of imaging devices capable of producing an image or a volume slice of the patient's body usable for planning and performing a navigated surgical procedure.

After a CT image is obtained of the patient, the target and an entry point are identified in the CT image by the medical personnel and from these points a linear trajectory for the surgical instrument is identified. This is often performed with the assistance of computer system controlled with appropriate software, which will calculate a pitch angle and a yaw angle with respect to a vertical gravity vector and a coordinate system relative to the CT scanner. The entry point is marked on the patient by known mapping techniques, such as with reference to a grid or other marker visible on both the patient and in the CT image. From the pitch and yaw angles, the trajectory may then be transferred from the image space to the actual patient space, and the surgical instrument can be aligned with respect to the entry point.

Thus, for example, in interventional radiology percutaneous needle placement under CT guidance is a state of the art procedure. The patient is positioned in a gantry of a CT scanner and several CT scans are obtained at different times during the procedure to localize the entry point and insert the needle to the target point in the body. Some exemplary applications include soft tissue biopsies (e.g. lung, liver, kidney), bone biopsies, vertebroplasty, RF ablation, etc. The procedure is typically performed with a straight needle-shape instrument. Localization of the entry point is generally less problematic than localization of the target point inside the patient. For entry point localization, the patient is typically scanned with a grid in the area of interest. The grid stripes are identified in the CT scan and are used to correlate the planned entry point as identified in the CT image with the physical entry point on the patient. For target point localization the physician usually has to align the angle manually according to the plan from the CT image and needs regular periodic scanning to monitor and control the trajectory. Thus guidance of the needle to the target is an iterative process with iterative control scans and often requires a revision of the needle trajectory path if the target is missed. This makes the procedure time consuming and yields a high amount of X-ray exposure to the patient and physician. Modern CT scanners provide a "CT-Fluoro" mode which allows constant imaging in a few slices. This feature allows the physician to visualize live the penetration of the needle into the tissue, but it also exposes the patient and staff to a high dosage of X-ray and allows only approaches in the axial plane of the CT ("in plane approach"). Often, however, an approach to the target in the plane of the CT scan is not possible, such as when a rib blocks the approach or when critical soft tissue would have to be penetrated.

Other known methods for aligning the surgical instrument in the patient space in the same orientation as planned in the CT image space are often cumbersome and/or require complex navigation systems.

Some systems use a surgical navigation system to help the surgical personnel guide a needle. For example, U.S. Patent Application Publication No. 2008/0200798, discloses a biopsy needle guide that has two independent arcuate angle guides to allow a guide tube to be pivoted about a single point and that is adapted to be adhesively attached to the skin of the patient. The needle guide is specially adapted to be visible in the CT scan image and also has specially adapted navigation markers that are tracked by a separate optical computer surgical navigation system in a manner known in the art. Images from the surgical navigation system are then registered with the CT scan images to allow the surgical staff to ensure that the needle guide is aligned on the patient in the orientation as defined in the CT scan image. In one embodiment, the biopsy needle guide is specially designed with spaced apart markers to help identify proper alignment with the CT scan image plane. Another needle guidance system based on an optical navigation system is disclosed in U.S. Pat. No. 7,876,942, in which an optical navigation camera is attached directly to a biopsy needle and a patch with fiducial markers is attached to the patient in the region of the selected entry point on the patient. Such systems, however, require complex optical surgical navigation systems in addition to CT imaging apparatus and usually require the attachment of tracking markers on the patient in order to be able to register the CT image with the patient.

In other systems, a biopsy needle is aligned in relation to the local vertical gravity vector without the use of an optical computer surgical navigation system. Some representative systems that operate on this principle are disclosed by U.S. Patent Application Publication No. 2005/0033315; EP 0 414 130; and EP 0 535 378. In these systems, generally, a bubble level or other mechanical leveling device is used to and maintain an alignment guide in a level plane, i.e., perpendicular to the local vertical gravity vector, so that a needle may be inserted at some defined trajectory angle while keeping the needle guide level. A drawback of these systems, however, is that the alignment guides must generally be maintained in the level condition and aligned in the plane of a perpendicular CT scan image plane in order to be able to accurately define the desired trajectory.

EP 1 977 704 discloses an alignment guide that uses pendulums to automatically identify the gravity vector in two, perpendicular planes so that the needle guide may be angularly adjusted in two independent, perpendicular planes. In this manner, the needle is adjusted about a yaw angle (transverse horizontal axis) by one set of pendulums, and has a protractor for adjusting the needle entry angle about the pitch angle (longitudinal horizontal axis). The alignment guide is designed to be held freehand by an operator and not to be attached to the patient. Again, a drawback of this system is that the alignment guide must be maintained at a particular level orientation in at least one degree of rotational freedom.

The inventors of the present invention have developed a system that can overcome at least some of the drawbacks of the previously known systems by eliminating the need for an external optical navigation system or the need to maintain the axial guide in particular the level plane before being able to calculate the desired trajectory in the patient space.

SUMMARY OF THE INVENTION

In one embodiment of the present invention a surgical trajectory guide to guide a medical device to a pivot point includes a base that can be attached to a patient in a fixed position. The trajectory guide also includes an axial guide member connected with the base and aligned with a pivot point along a first axis in fixed relation to the base and a second axis perpendicular to the first axis. The guide member has a longitudinal axis, and the connection between the base and the axial guide member is such that the longitudinal axis always passes through the pivot point, and such that the axial guide member is prevented from rotating around the longitudinal axis. The trajectory guide further includes at least one electronic angle sensor associated with the axial guide member and adapted to automatically sense a first angle of the axial guide member relative to the local gravity vector about the first axis and a second angle of the axial guide member relative to the local gravity vector about the second axis without having to level the base.

A second embodiment of the present invention is a method of guiding an axial medical instrument during a procedure that includes the step of placing a trajectory guide having an axial guide member on a patient so that a first axis of the trajectory guide is aligned with a predetermined axis of an imaging device, wherein the axial guide member has a longitudinal axis that pass through a pivot point on the first axis and wherein the axial guide member is prevented from rotating around the longitudinal axis. The method also includes the step of adjusting the axial guide member so that the longitudinal axis is located on a planned trajectory for the axial medical instrument. Finally, the method includes the step of placing the axial surgical instrument in the axial guide member to perform the medical procedure Other aspects and advantages of the present invention will become apparent upon consideration of the following detailed description.

DETAILED DESCRIPTION

Figure 1:
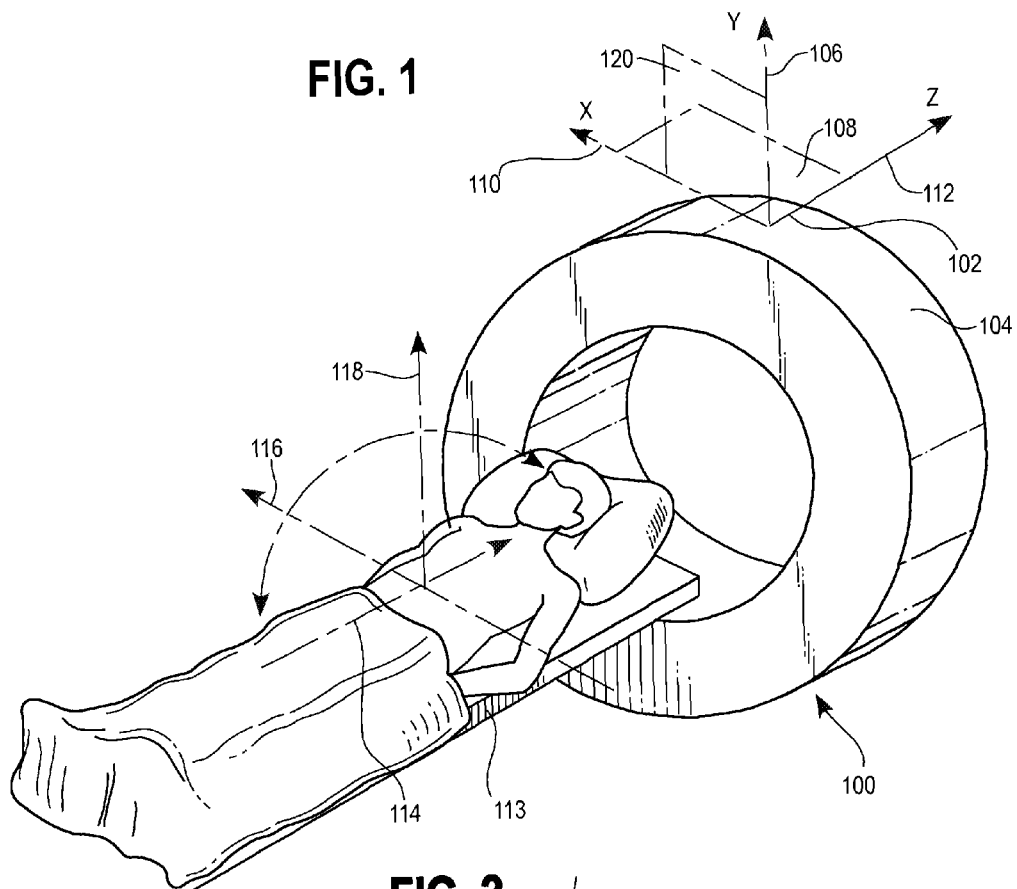
FIG. 1 is a schematic view of a patient operatively positioned in a CT scanner showing the basic parts of the CT scanner and coordinate frames.
Figure 3:
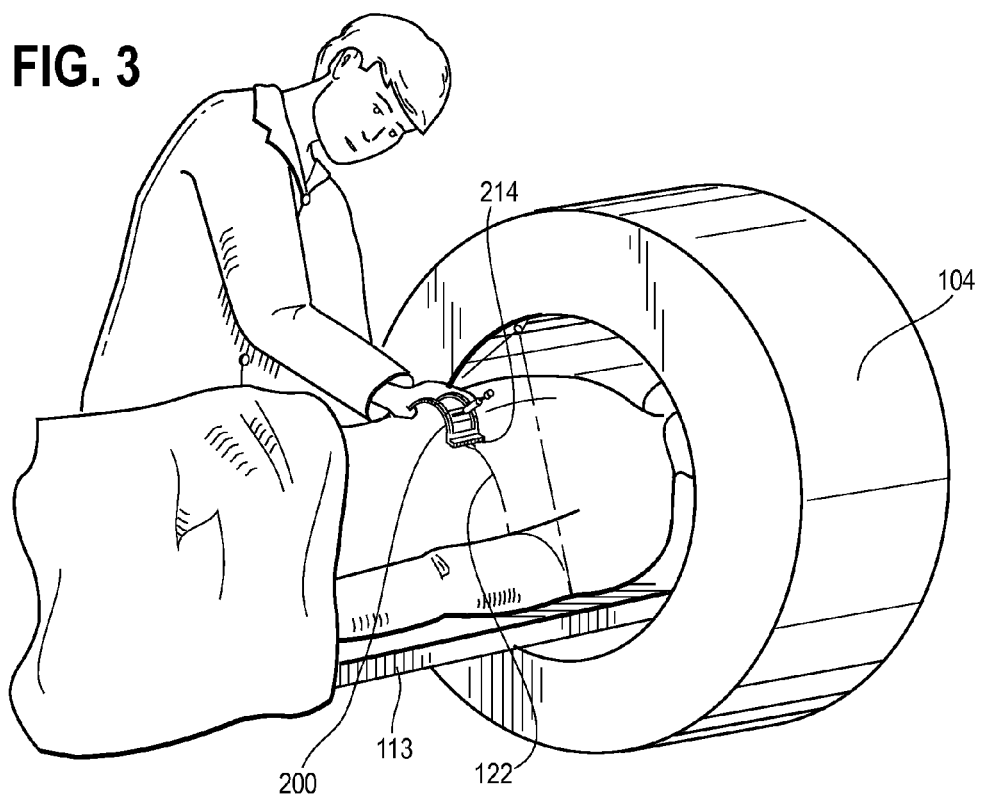
FIG. 3 shows an operator positioning a trajectory guide of the invention on a patient in the CT scanner according to an aspect of the invention.

When conducting a surgical procedure, such as a biopsy, with the assistance of a computed topographic (CT) guidance system, some basic assumptions may often be made about the setup of the CT scanner that can aid in navigation of surgical tools, such as a biopsy needle, for example. As shown in FIG. 1, A CT scanner 100 customarily has a coordinate system 102, or CT coordinate space, associated with a gantry 104 for use in navigation and other spatial calculations that may be required for beneficial use of the CT scanner 100 and associated CT image data (not shown). Specifically, it is customary to set up the CT scanner gantry 104 in a "level" orientation. In other words, the vertical Y-axis 106 of the CT coordinate space 102 of the CT scanner 100, is parallel to the local gravity vector (not shown), and the X-Z plane 108 of the CT coordinate space formed by the X-axis 110 and the Z-axis 112 is level in that it is perpendicular to the vertical Y-axis. If the Z-axis 112 is the axis parallel with the longitudinal axis 114 of a patient couch 113 mounted on the gantry 104 of the CT scanner 100, the patient transverse axis 116 is the axis transverse to the longitudinal axis 114 of the patient couch 113, and the patient sagittal axis 118 is the vertical axis through the gantry 104, then yaw represents the angle of rotation around the longitudinal axis 114 (i.e., rotation of the patient toward the patient's right side or left side) with respect to the sagittal axis 118, and pitch represents the angle rotation around the transverse axis 116 (i.e., rotation of the patient toward the patient's head or feet) with respect to the sagittal axis. Under these conditions where the patient and CT scanner axis are parallel to each other, yaw and pitch can be automatically correlated with the local gravity vector. These angles are given in the coordinate system of the leveled CT scanner 100. As shown in FIG. 3, typical CT scanners have a laser that marks a line 122 that is parallel to the X-axis 110 and located on the (X-Y) plane 120 of the CT scanner 100. For convenience, these coordinate references will be used throughout the following description with the understanding that the invention is not dependent on the specific orientations or types of coordinate system used. Also, so long as the patient is immobilized and does not move relative to the couch 113, the patient axes can be ignored in any of the computations described as follows.

One aspect of the disclosed system relates to guiding a needle-like instrument in an interventional radiology procedure under CT guidance. X-ray tomography, magnetic resonance (MR) guidance, or other similar image modality devices that produce dimensional image data output, either 2D or 3D, usable in a similar manner also could be used, and the term "CT" will be used throughout to refer to all such modalities that can provide the necessary image data functionality unless otherwise specified. An entry point is identified and marked on the patient's body in the conventional way, such as by grid on the patient that is visible in CT images obtained by the CT scanner. A navigated alignment tool for defining a trajectory for an axial instrument, or "trajectory guide," has sensors that allow the needle to be aligned to the desired trajectory. After a first CT scan (diagnostic scan) is acquired on the CT console computer, the entry point, the target point, and from these the trajectory is defined on the computer and preferably shown on a display screen. With the entry point identified, the only remaining degrees of freedom for complete definition of the trajectory are the two angles, yaw and pitch, which are assumed to be output by the CT console computer in a conventional manner. Of course, other computers not on the CT scanner may be used, and the term console computer is meant to encompass any such computer.

Figure 2:
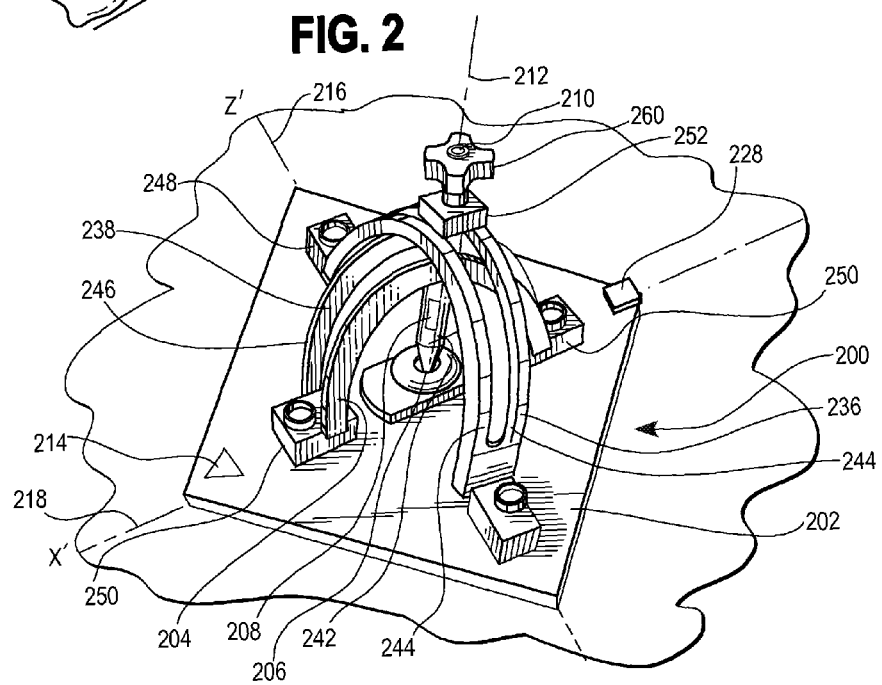
FIG. 2 is an isometric view of an embodiment of a trajectory guide according to the invention having an angular adjustment mechanism including two orthogonally aligned arcuate angular guides

One embodiment of the present invention includes a "trajectory guide" with an axial guiding sleeve that has an integrated angle sensor, such as a sensor based on micro-chip MEMS (micro electrical mechanical sensor) technology. FIG. 2 shows a depiction of a first embodiment of a trajectory guide. The trajectory guide 200 has a base 202 that is adapted to be placed against the patient's skin at the entry point, a guiding sleeve 204 pivots independently about two degrees of freedom through a pivot point 206, and an integrated angle sensor 208 that measures the angle of the guiding sleeve 204 with respect to the local vertical gravity vector. The base 202 is preferably a flat planar member, such as a plate or ring; however the base may be other shapes capable of being placed against the patient and preferably maintaining the trajectory guide in a stable aligned position as discussed below. The base 202 has an aperture (not visible) therethrough and encompassing the pivot point 206. The sleeve 204 has an aperture 210 that is sized to allow selected surgical tools, such as a biopsy needle, probe, or other axial device (not shown), to extend therethrough. The sleeve 204 has a longitudinal axis 212 that can be adjusted in two degrees of freedom by angular pivoting about the X'-axis (i.e., pitch) and angular pivoting about the Z'-axis (i.e., yaw) as depicted in the drawings. The angle sensor 208 automatically measures the angle of the longitudinal axis 212 of the trajectory guide 200 relative to the local gravity vector and outputs digital angular data representative of the measurement values. The angle sensor 208 in this embodiment is integrated into the guiding sleeve 204 of the trajectory guide 200. Because the angle sensor 208 measures the angle relative to the local gravity vector, it is not necessary that the base 202 be level and the base can be at any angle relative to gravity so long as the base is aligned with the X'-axis. By measuring the angle of the longitudinal axis 212 relative to the local gravity vector and by preventing rotation of the guiding sleeve 204 about the longitudinal axis 214, the alignment of the guiding sleeve 204, namely the pitch relative to the axial plane 120 and the yaw relative to the sagittal plane (Y-Z) of the CT scanner 100, can be determined.

The angle sensor 208 preferably includes a MEMS angle sensor that digitally senses the change of the angle of the sensor 208 with respect to local gravity such that a single sensor can detect changes in both the pitch and yaw of the guiding sleeve 204. If the angle sensor 208 is aligned perpendicular to the longitudinal axis 214 of the guiding sleeve 204 and is aligned parallel to either the X-axis 110 or the Z-axis 112 of the CT device 100, then the data relative to the pitch and yaw of the guiding sleeve 204 will directly relate to the coordinate system of the CT device 100 and therefore to the coordinate system of the patient. This will enable the determination of the approach to the target point within the patient simply and without having to constantly take X-rays or other scans of the patient, thus minimizing radiation exposure of both the patient and operator. The trajectory guide 200 has an appropriate data interface 228 to transfer data from the sensor 208 such as a data port for wires or a wireless transmitter or transceiver, to allow the console computer to obtain the digital angular data for use in navigation and/or planning routines executed therein. As will be discussed later, the display can also have an integrated angle sensor to directly display the data to the operator.

The base 202 preferably includes one or more markers 214 aligned with one or both of an X'-axis 218 and a Z'-axis 216 of the trajectory guide 200, both of which extend through the pivot point 206 about which the guiding sleeve 204 rotates in the pitch and yaw degrees of freedom. The pivot point 206 is in a fixed position with respect to the base 202 and is designed to be placed directly on top of the entry point on the patient such that the pivot point 206 can be substantially coterminous with the entry point during use of the trajectory guide 200. Thus, a guide path through the guiding sleeve 204 along longitudinal axis 212 extends through the pivot point 206 at every angular position of the guiding sleeve 204 and through the entry point on the patient when appropriately placed on the patient.

Thus, it is important that the rotational movement of the guiding sleeve 204 about its longitudinal axis 212 with the base is prevented. This may be accomplished in many different ways, a few of which are described in relation to various embodiments disclosed herein. This allows the angle sensor 208, for example, to differentiate between movement around the X-axis 110 of the CT scanner and movement around the Z-axis 112 of the CT scanner. With this restraint on rotation of the guiding sleeve 204 about its longitudinal axis 212, calibration (or registration) of the trajectory guide is not needed. The angle sensor 208 is always referencing gravity, and is thus automatically in registration with the Y-axis 106 of the CT scanner. A simple ball-and-socket joint would not be sufficient without adding additional calibration or registration steps if rotational movement of the guiding sleeve is not prevented.

The trajectory guide 200 also includes an angular adjustment mechanism including an outer angular guide 236 and an inner angular guide 238 disposed orthogonally to each other and aligned in the X'-Y' and Z'-Y' planes, respectively. The guiding sleeve 204 is in the form of an elongate hollow open-ended tube 242 and is attached to the base 202 in a manner that allows the guiding sleeve 204 to move relative to the base over the aperture through the base 202. The connection between the base 202 and the guiding sleeve 204 can be any suitable joint or connection such as but not limited to a ball-and-socket joint (not shown). Each of angular guides 236 and 238 is in the form of a pair of parallel spaced apart semi-circular rails 244 and 246 that are pivotably attached to the base 202 with two pivot connections 248 and 250 that are aligned with the respective X' or Z'-axes. The rails 246 of the inner angular guide 238 are disposed radially inwardly from the rails 244 of the outer angular guide 236 such that the inner and outer angular guides can slide independently across each other. A carriage member 252 is slidably attached to each of the angular guides 236 and 238, and to a top end of the guiding sleeve 204. The carriage member 252 slides independently between and along each of the inner and outer angular guides 236 and 238 such that the guiding sleeve 204 pivots independently in pitch and yaw about the intersection of the X'-axis and the Z'-axis, which defines the pivot point of the guiding sleeve 204. Thus, the longitudinal axis 212 of the guiding sleeve 204 is always aligned through the pivot point, and a needle or other axial instrument that is inserted into the aperture 210 of the alignment guide 204 will always be aligned to project through the guiding sleeve 204 into the entry point when the pivot point is placed on top of the entry point on the patient. The carriage member 252 is preferably fixedly secured with the guiding sleeve and prevents the guiding sleeve from rotating about its own longitudinal axis 210. The carriage member 252 may optionally include a locking mechanism 260, such as a cam or screw-type lock, to lock the guiding sleeve 204 in a selected orientation. Alternatively or additionally, each angular guide may have its own locking member to allow independent locking of each angular guide.

Preferably, the trajectory guide 200 is manually rotated by the operator such that X'-axis 218 lies on the X-axis 110 of the CT scanner using a laser projection of the CT scanner that projects a line 122. With the angle sensor aligned with the X'-axis 218 of the trajectory guide 200 and parallel to the X-axis 110 of the CT scanner 100, the sensor 208 is able to measure two independent angles (i.e., two degrees of freedom): yaw as the angle around the Z-axis 112 of the CT scanner 100, and pitch as the angle around the X-axis 110 of the CT scanner 100, which are the same angles used during planning in the CT scan data on the console computer. As long as the X'-axis 218 of the trajectory guide 200 is aligned with the X-axis 110 of the CT scanner 100, the trajectory guide 200 does not have to be leveled in the horizontal plane, i.e. the base of the trajectory guide does not have to be "level" on the patient. Because the patient has been immobilized on the CT couch 113, the alignment of the trajectory guide 200 to line 122 will also align the guide 200 with the axial and transverse axes of the patient. This provides a significant benefit over the various trajectory guides that require the guide to be maintained in some level condition in order to obtain the desired planned trajectory.

In addition the guiding sleeve 204 can either be easily replaced by a guiding sleeve with a different diameter and/or shape to accommodate a different instrument or can be fitted with inserts to accommodate different shaped instruments.

The console computer can use the angular data received from the trajectory guide 200 to calculate the trajectory of the guiding sleeve 204 with respect to the Y-axis 106 of the CT scanner in the pitch and yaw degrees of freedom, i.e. gravity or local vertical, and display a representation of the trajectory in a usable manner on the display device, such as being overlaid on the CT image or other visualization useful for assisting the operator to place the guide sleeve in a desired trajectory.

To accomplish this, an operator, such as a surgeon or radiologist, positions the trajectory guide 200 with the pivot point 206 directly on top of the selected entry point marked on the patient and aligns the trajectory guide 200 in rotation such that the reference marks 214 on the trajectory guide 200 are aligned with the horizontal axis, e.g., the X-axis 110 or the Z-axis 112 of the gantry plane of the CT scanner 100. Preferably, as shown in FIG. 3, the reference marks on the trajectory guide 200 corresponding to the X'-axis are aligned with a laser beam 122 from the CT scanner 100 which projects a line on the patient that also lies on the axial plane 120 of the scanner 100 as is common for most CT scanners. The trajectory guide 200 is fixed in position to the patient in this aligned state, such as with adhesive stickers (not shown) on the bottom of the trajectory guide 200. Of course other attachment mechanisms, such as straps or hook-and-loop fasteners may be used. Alternatively, the trajectory guide may not include a fastener for affixing the base to the patient, and the operator could hold the trajectory guide in the aligned state. In any event, maintaining the trajectory guide in the aligned state on the patient also allows the patient to be moved out of the CT gantry 104 on the patient couch 113 and allows the procedure to be performed outside of the CT gantry provided the orientation of the patient does not change relative to the coordinate system of the CT scanner 100. Rotational pre-alignment of the trajectory guide with the X-axis 110 or Z-axis 112 of the CT scanner 100 together with the fact that the patient couch 113 has a known alignment with respect to gravity, i.e., the Y-axis 106, realizes an angular registration between the CT coordinate system 102 and the patient on the patient couch 113 which obviates the need for additional registration between the coordinate system of the CT scanner 100 and CT image data and the coordinate system of the patient.

Figure 4:
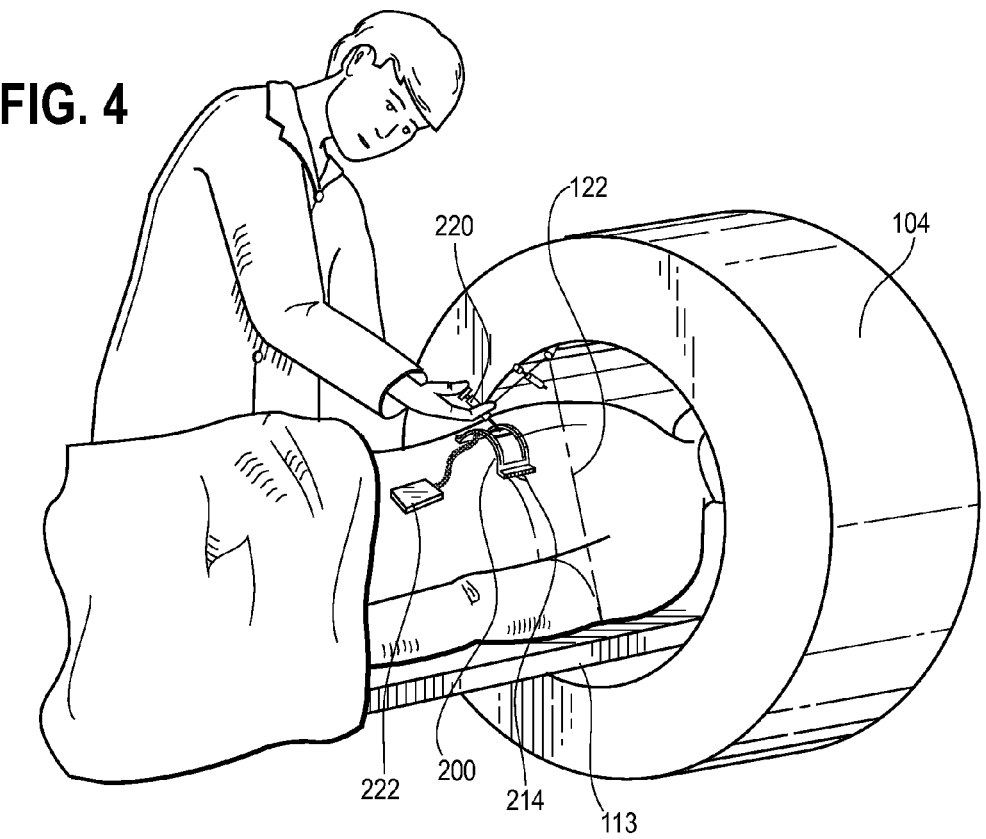
FIG. 4 shows the operator adjusting alignment of the trajectory guide to match a pre-selected trajectory according to an aspect of the invention.

After the trajectory guide has been aligned with the X-axis 110, the operator inserts a needle or some other instrument 220 into the guiding sleeve 204 of the trajectory guide 200 as shown in FIG. 4. The trajectory guide 200 has a data interface operatively coupled with a display unit 222 which displays the current angular positions of the needle 220 in the CT coordinate system 102, i.e. the two angles yaw and pitch. The operator can now change the angular positions of the needle 220 in the alignment unit to match them with the target angles for the plan in the CT image, e.g. match yaw and pitch with the planned values, thereby achieving alignment of the guiding sleeve 204 with the planned virtual alignment calculated by the console computer.

The display can visually assist the operator achieve such alignment in any of numerous modes. For example, and with reference to FIG. 10, the display 222 may be in the form of a "target" view 224 along the axis of the planned trajectory normal to a plane perpendicular to the axis of the planned trajectory, wherein the axis of the planned trajectory is at the center of the "target" and an actual trajectory 226 of the axis of the guiding sleeve is displayed as being offset from the target trajectory an amount proportional to the angular misalignment. Thus, when the actual trajectory 226 is aligned with the planned trajectory, the axis of the guiding sleeve 204 is aligned with the center of the target. Other methods of visually displaying the actual alignment of the guiding sleeve in relation to the planned trajectory are also contemplated. For example, a classic two-window view, one of the X-Y plane and one of the Z-Y plane, may be used, and other display modes could be used in a manner readily understood by a person of skill in the art, including display of numerical values for pitch and yaw.

Once the guiding sleeve 204 is aligned with the planned trajectory the guiding sleeve 204 is locked into the selected alignment by appropriate locking mechanisms, and the operator can insert the needle into the body to obtain the biopsy in any acceptable manner or perform the other procedures with similar longitudinal instruments. For depth control of the needle or instrument, conventional references are used, e.g. calibrated distance marks on the needle that allows the needle to be inserted to a pre-calculated targeted depth in a manner well known in the art.

In one embodiment, the trajectory guide also serves as a needle holder in case control scans are needed to verify the position of the needle in the body. For example, the guiding sleeve 204 may include a mechanism for clamping or otherwise maintaining the needle at a selected depth in the guiding sleeve. Alternatively, the needle may be maintained in place by frictional contact with the patient and the sleeve may simply maintain the needle in the selected trajectory. This functionality can overcome the need for the operator to hold the needle during scanning or can prevent the needle from bending under its own weight if not held separately by the operator. The trajectory guide also can minimize the risk of the needle bending during insertion by using an elongate tubular member for the guiding sleeve, which can maintain the needle in a straight line at least within the sleeve. A longer guiding sleeve 204 may be used to provide increased bending resistance. Different diameters of guiding sleeves may be provided to accommodate compatibility to various needles thus making the trajectory guide an open platform.

Figure 9:
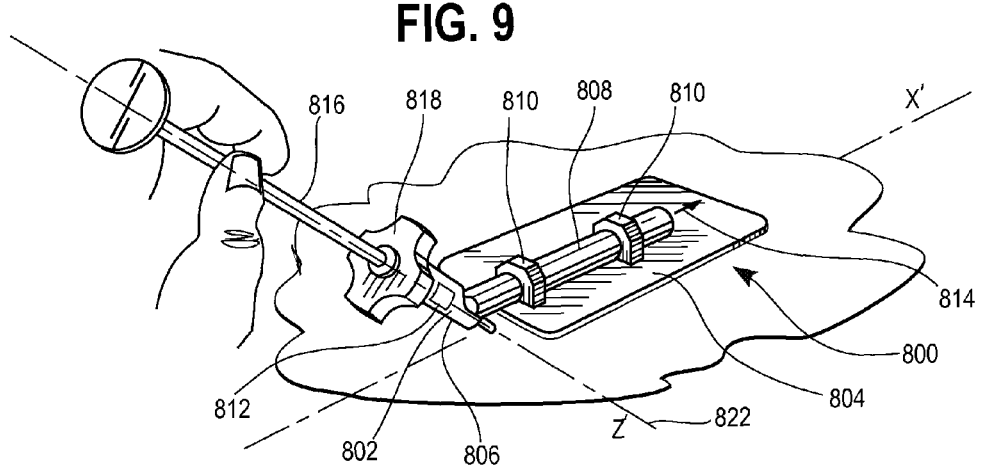
FIG. 9 is an isometric view of an additional embodiment of the trajectory guide having an angular adjustment mechanism in the form of a hinge joint.
Figure 10:
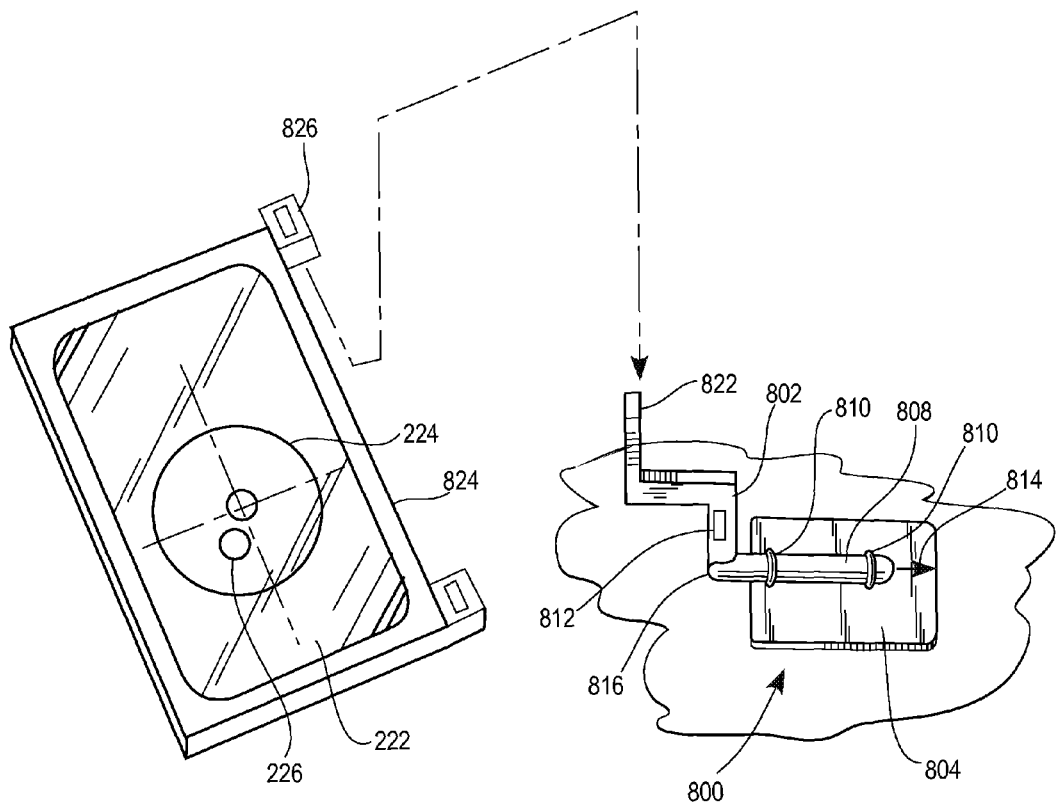
FIG. 10 is an isometric view of yet a further embodiment of the trajectory guide including a docking mechanism for attachment of a portable display device that includes an integrated angle sensor.

In several specific embodiments, different mechanical concepts are employed to control pitch and yaw adjustment and prevent rotational movement of the guiding sleeve about its longitudinal axis, which ensures that the angles measured by the angle sensor associated with the guiding sleeve are independent and reference the corresponding angle sin of the CT scanner coordinate system. Such concepts can be achieved by but are not limited to some specific embodiments as shown in the drawings, including designs that use: one guide arc with a rail that moves along the arc (FIG. 5), a ball socket joint with an arm locking the rotational movement of the sleeve (FIGS. 6 and 11), hemispherical mechanics (FIG. 7), translation stages (FIG. 8), and a hinge-joint (FIGS. 9 and 10). These specific actualizations will be described in detail hereafter.

Figure 5:
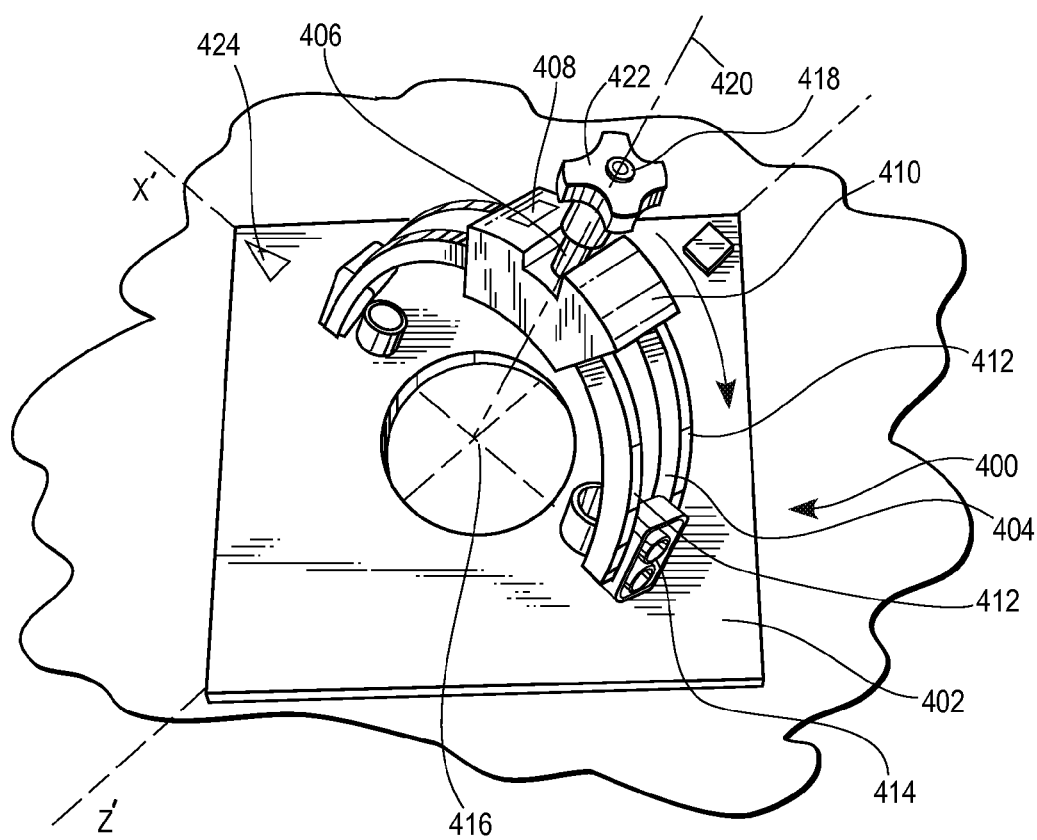
FIG. 5 is an isometric view of another embodiment of the trajectory guide having an angular adjustment mechanism including a single arcuate angular guide and a carriage that slides independently on the arcuate angular guide.

With reference to FIG. 5, another variation 400 of the trajectory guide 200 is shown, which is generally similar to the trajectory guide 200 of FIG. 2 except that there is only one arcuate angular guide 404 pivotably attached to a base 402 using pivoting connections 414 and a guiding sleeve 406 that is not attached to the base 402. Further, in this embodiment, an angle sensor 408 is secured to a slidable carriage 410 and preferably is integral therewith. The arcuate angular guide 404 is aligned to pivot about the X'-axis and rails 412 of the arcuate angular guide 404 have a single radius aligned with the X'-axis. Consequently the slidable carriage 410 pivots about a pivot point in two degrees of freedom by pivoting the arcuate angular guide about the pivot connections to the base about the X'-axis and by sliding the slidable carriage 410 along the rails 412 of the arcuate angular guide 404 about the Z'-axis. The guiding sleeve 406 is carried by the slidable carriage 410 and defines a through bore 418, such as with a tubular member, which is longitudinally aligned with the pivot point 416, whereby the axis 420 of the through bore 418 is always directed through the pivot point 416 regardless of the position of the slidable carriage 410. One or more angle sensors 408, such as a MEMS level sensor, are fixedly associated with the guiding sleeve in a manner adapted to automatically provide pitch and yaw angular measurement data, and a data interface is operatively connected with the angle sensor to allow transmission of the angular measurement data to a console computer in a manner substantially as described previously herein. Again, appropriate locking mechanisms 422 may be used to lock the instrument inserted into bore 418 at a selected depth. In addition, visible markers 424 are disposed on the base and aligned with one or both of the X' and Z' axes in order to enable alignment of the trajectory guide with the X and/or Z axes of the CT scanner as described previously. Because the area under the rails 412 is open, this affords the operator with a direct visual view of the entry point of the instrument that has been inserted in the guiding sleeve 406 into the body of the patient.

In a further embodiment, if the pivoting connections 414 are removed and replaced by connections tht hold rails 412 perpendicular to the base 402, then this device will allow the guiding sleeve 406 to be moved along the plane and allow the guiding sleeve 406 to move in the yaw direction only as the pitch is fixed to a single plane. This variation can be useful for certain procedures where the device will be inserted along the X-Y plane 120.

Figure 6:
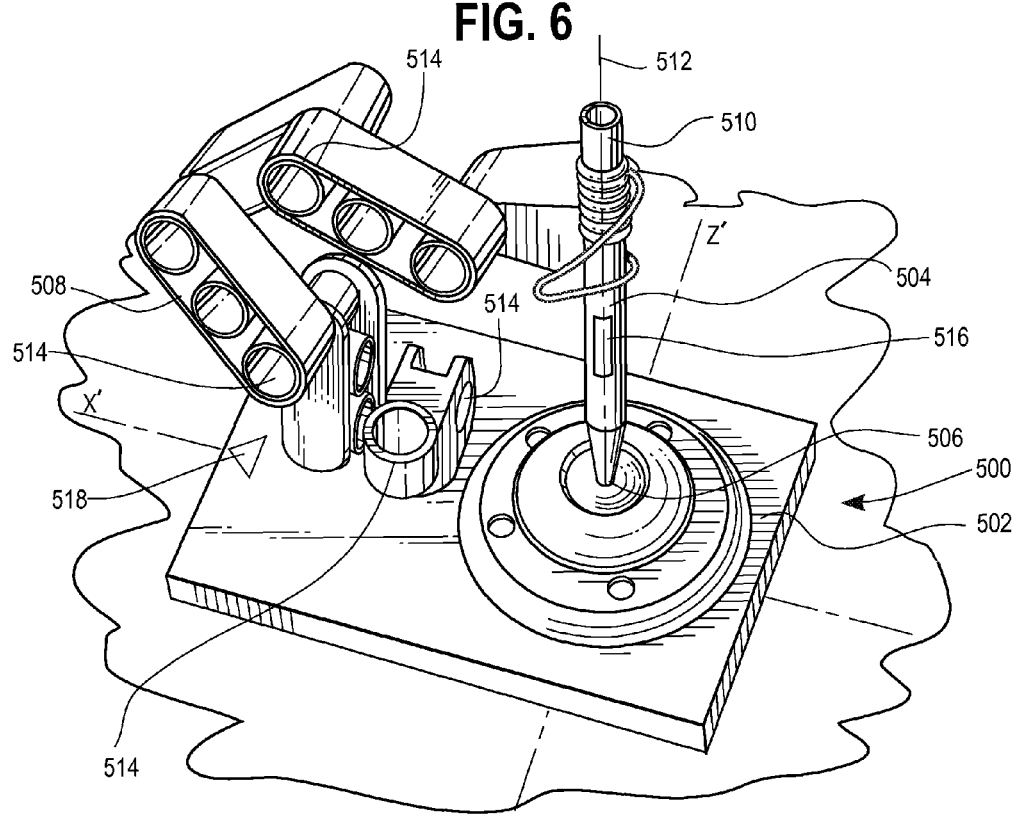
FIG. 6 is an isometric view of a further embodiment of the trajectory guide having an angular adjust mechanism including a linkage connected to the base and the guiding sleeve.

Turning to FIG. 6, in another variation 500 of the trajectory guide 200, the guiding sleeve 504 is attached to the base 502 with a ball-and-socket connection 506. In order to prevent the guiding sleeve 504 from rotation about its longitudinal axis 512, a linking mechanism 508 is attached to the distal end 510 of the guiding sleeve 504 and to the base 502. The linking mechanism 508 includes one or more pivot joints 514 sufficient to allow the guiding sleeve 504 to be pivoted in two degrees of freedom, i.e., pitch and yaw, about the pivot point in a manner clear to a person of skill in the art. The trajectory guide 500 includes one or more angle sensors 516 fixedly associated with the guiding sleeve 504 in any manner as previously described herein sufficient to provide automatic pitch and yaw angle measurements in relation to gravity and an appropriate data interface sufficient for providing the angle measurements to an external computer. Appropriate locking mechanisms may be used to secure the linking mechanism 508 and guiding sleeve 504 in a selected trajectory in a manner clear to a person of skill in the art. In addition, one or more visible markers 518 are disposed on the base and aligned with one or both of the X' and Z' axes in order to enable alignment of the trajectory guide 500 with the X and/or Z axes 110, 112 of the CT scanner 100 as described previously.

Figure 7A:
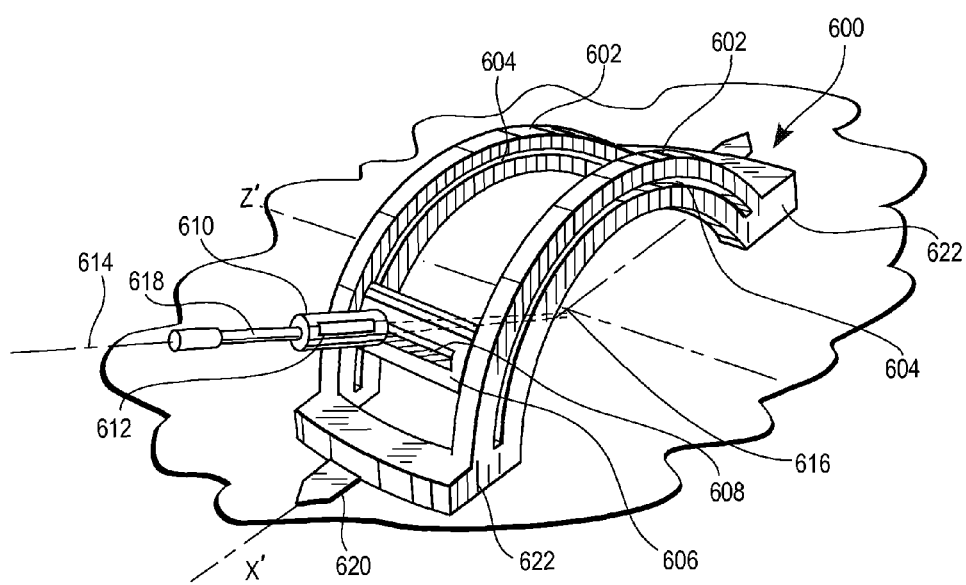
FIGS. 7*a*-7*d* are views of yet another embodiment of the trajectory guide having an angular adjustment mechanism in a hemispherical arrangement.
Figure 7B:
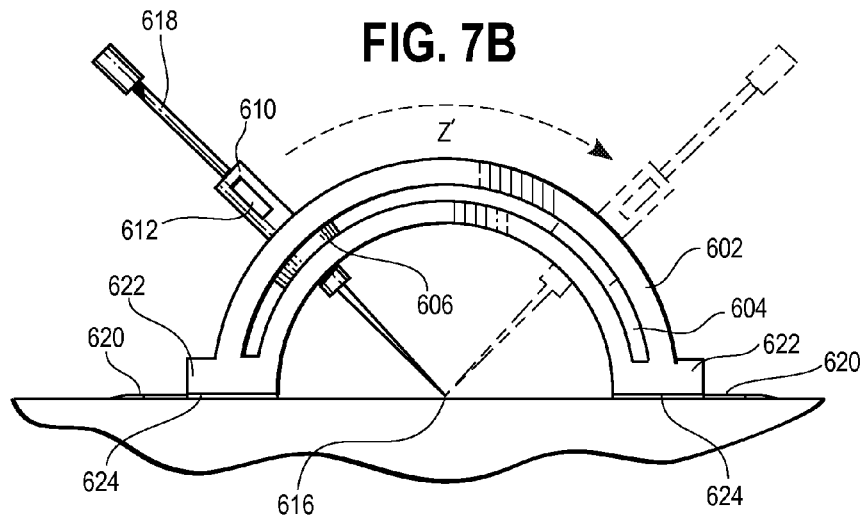
Figure 7C:
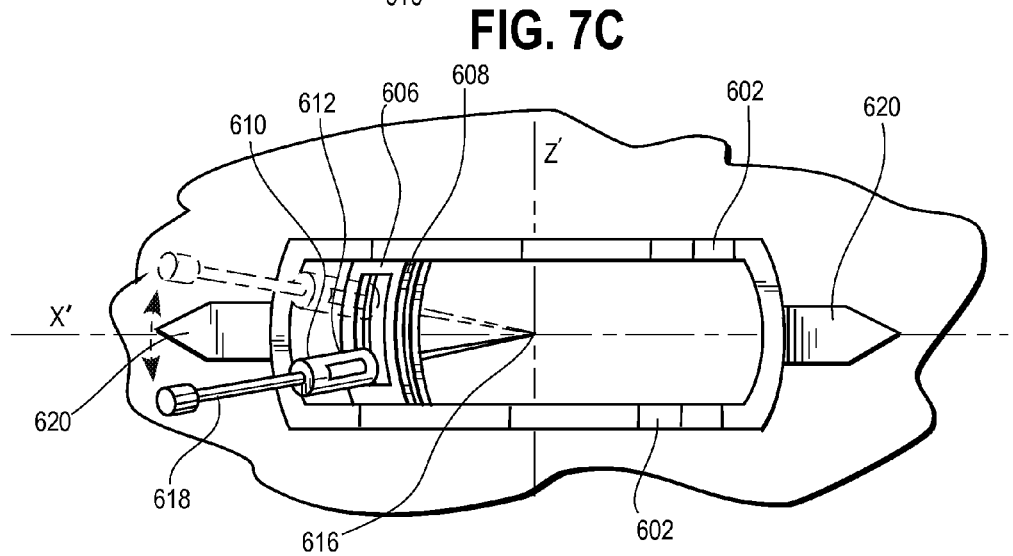
Figure 7D:
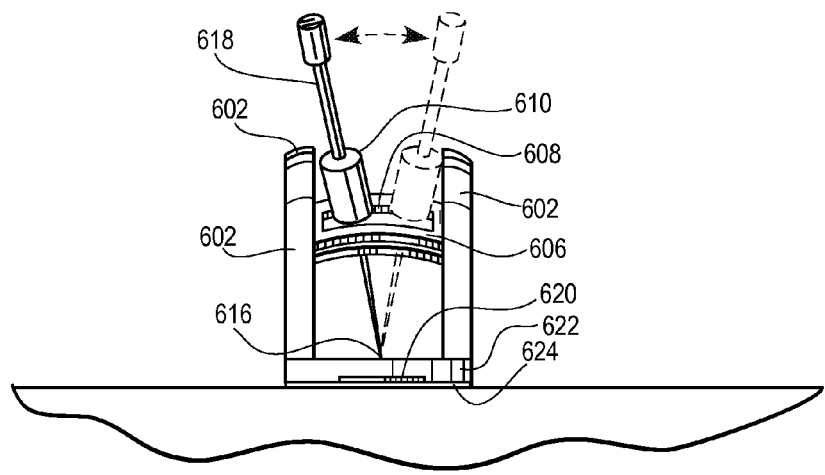

FIGS. 7a-d show yet a further variation 600 of the trajectory guide 200. In this embodiment, the guiding mechanism consists of a pair of orthogonally oriented arcuate angular guides 602 that have a pair of slots 604. A carriage member 606 in the shape of a hemispherical segment is movably mounted in the slots 604 defining arcuate rails. The carriage member 606 includes an elongate slot 608 that is perpendicular to arcuate angular guides 602. A guiding sleeve 610 is attached to the carriage member 606 and can slide within slot 608 as shown in FIG. 7C. An angle sensor 612 is mounted on the guiding sleeve 610. The pair of spaced apart arcuate guides 602 are parallel to and aligned with the X'-axis of guide 600. The arcuate rails 604 in spaced apart arcuate guides 602 are shaped as or otherwise define circular arc segments. The carriage member 606 is carried by and between the arcuate rails 604 and slides thereon. The guiding sleeve 610 is fixed within the slot 608 such that the guiding sleeve 610 can slide within slot 608. The arcuate shape of the carriage member 606 projects a longitudinal axis 614 of the guiding sleeve through a pivot point 616. A needle 618 or other similar device inserted through the guiding sleeve 610 will pass though the pivot point 616. The interface between the guiding sleeve 610 and the slot 608 prevents the guiding sleeve 610 from rotating about its longitudinal axis 614. In this manner, sliding the carriage member 606 along the arcuate rails 604 as shown in FIG. 7B pivots the guiding sleeve 610 about the pivot point 616 in the yaw degree of freedom, and sliding the guiding sleeve 610 back and forth in the slot as shown in FIGS. 7C and 7D pivots the guiding sleeve 610 about the pivot point 616 in the pitch degree of freedom. An angle sensor 612 is preferably integrally connected with the guiding sleeve 610 in a manner as described previously sufficient to allow the angle sensor to automatically sense the pitch and yaw angular measurements of the guiding sleeve 610, and an appropriate data interface allows the angular measurements to be directed to a console computer as discussed previously herein. In addition, visible markers 620 are disposed on a base 622 and aligned with one or both of the X' and Z' axes in order to enable alignment of the trajectory guide with the X and/or Z axes of the CT scanner as described previously. As shown in FIGS. 7B and 7D, an adhesive 624 can be used to secure the trajectory guide 600 to the patient.

Figure 8:
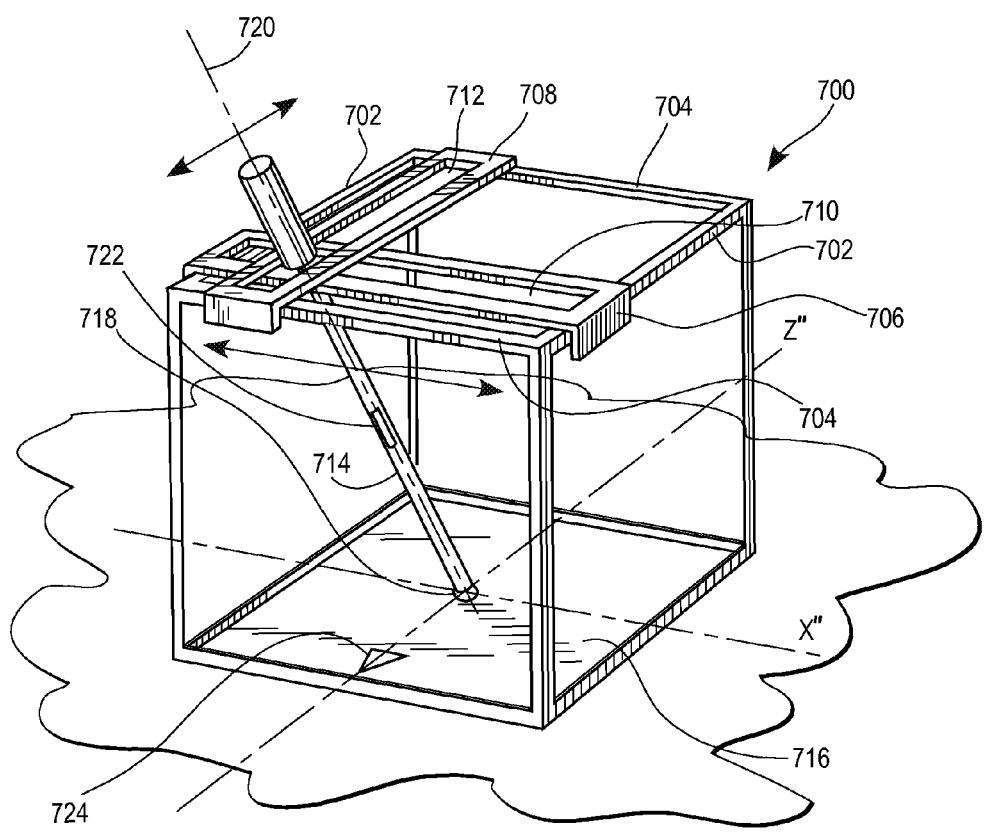
FIG. 8 is an isometric view of a still further embodiment of the trajectory guide having an angular adjustment mechanism that prevents rotation about the longitudinal axis.

In FIG. 8, another variation 700 of the trajectory guide 200 is shown in which the trajectory guide 700 include a first set of parallel rails 702 and a second set of parallel rails 704 that are perpendicular to the set of rails 702. A first carriage 706 is mounted on rails 702 and a second carriage 708 is mounted on rails 704. Carriages 706 and 708 can slide along respective rails 702 and 704. Each of carriages 706 and 708 has a slot 710 and 712 that overlap at orthogonal angles. A guiding sleeve 714 is mounted within slots 710 and 712 so that the guiding sleeve 714 can slide within slots 710 and 712 and carriages 706 and 708 can slide on rails 702 and 704. The elongate slot 710 in the first carriage 706 is aligned parallel with the X'-axis and the first carriage 706 is slidably carried by rails 702 that are attached to a base 716. The carriage 706 slides back and forth parallel to the Z'-axis. The elongate slot 712 in the second carriage 708 is aligned parallel with the Z'-axis. Carriage 708 is slidably carried by rails 712 attached to the base 716 that allow the carriage 708 to slide back and forth parallel to the X'-axis. The guiding sleeve 714 extends from a ball-and-socket joint 718 mounted on the base 716 up through each of the slots. In this embodiment, the carriages 706 and 708 are disposed in a planar arrangement and translate in the X'-Z' plane along the X' and Z' axes. The guiding sleeve 714 slides along each slot, but is restrained from pivoting about its longitudinal axis 720 by the guiding sleeve's interface with the two slots. For example, the outer surface of the guiding sleeve 714 may be square and engage directly against the slots such that the slots prevent the guiding sleeve 714 from rotating. Other mechanisms for preventing rotation of the guiding sleeve 714 about its longitudinal axis 720 may also be used. The angle sensor 722 is preferably integrally connected with the guiding sleeve 714 in a manner as described previously sufficient to allow the angle sensor 722 to automatically sense the pitch and yaw angular measurements of the guiding sleeve 714, and an appropriate data interface allows the angular measurements to be directed to a computer system as discussed previously herein. In addition, at least one visible marker 724 is disposed on the base 716 and aligned with one or both of the X' and Z' axes in order to enable alignment of the trajectory guide with the X and/or Z axes of the CT scanner as described previously.

FIG. 9 shows a further variation 800 of the trajectory guide 200 in which the guide sleeve 802 is attached to a base 804 in a manner that allows pivoting about only two orthogonal axes. The base 804 is in the form of a sticker that attaches to the body of the patient. The guiding sleeve 802 is attached to the base 804 with a hinge joint 806 and a rod 808 that is attached to the base 804 by two members 810 such that the rod 808 can rotate around its longitudinal axis. The combination of the hinge joint 806 and the rotation of the rod 808 only allows pivoting of the guiding sleeve 802 in the pitch and yaw directions with respect to the X' and Z' axes of the base 804. The base 804 when attached to the patient prohibits rotation of the trajectory guide 800 about the Y-axis of the patient (i.e., roll) and the hinge joint 804 to move in a plane that includes the X' axis. The length axis of the rod 808 is also aligned with the CT gantry to be parallel to the XY-plane 120 of the laser line 122 of the CT gantry 104. Then the degree of freedom of the hinge joint 804 represents yaw rotation relative to the patient. The rotation around the length axis of the rod 808 represents pitch rotation relative to the patient. An angle sensor 812, preferably a MEMS angle sensor, is disposed integrally on the guiding sleeve 802 in an orientation that is parallel to the length axis of the rod 808 and therefore can determine the absolute angle of the guiding sleeve 802 with respect to gravity. The data interface (not shown) allows the angular measurements to be directed to a computer system as discussed previously herein. In addition, at least one visible marker 814 is disposed on the base 804 and aligned with one or both of the X' and Z' axes in order to enable alignment of the trajectory guide with the X and/or Z axes of the CT scanner as described previously. A needle 816 can be inserted through the guiding sleeve 802 and lock 818 is used to lock the insertion depth of the needle.

Turning now to FIG. 10, a variation of the trajectory guide 800 includes a docking feature 822 connected with the guiding sleeve 802, wherein a handheld computer and monitor 824 unit may be attached to the docking feature 822 by a quick-release interface 826 with the docking feature 822. The quick-release interface 826 combined with the docking feature 822 preferably prevents rotation of the monitor unit 824 with respect to the guiding sleeve 802. For example, as shown in FIG. 10, the docking feature 822 can include a square pin and the quick release 826 can include a square bore that receives the square pin therein. Although the docking feature 822 is shown on a trajectory guide similar to the trajectory guide of FIG. 9, the features for connecting the handheld computer and monitor unit with the trajectory guide may be readily adapted for use with any trajectory guide of the invention.

In one embodiment, the handheld computer and monitor unit includes the software necessary to compute the pitch and yaw alignment of the axis of the guiding sleeve and display the alignment superimposed with the planned trajectory. In the embodiment shown in FIG. 10, the display shows the alignment in a view along the axis of the planned trajectory plane perpendicular to the planned trajectory. The position of the axis of the guiding sleeve is shown in the same plane relative to the axis of the planned trajectory. In one arrangement, the planned trajectory is shown maintained at the intersection of the cross-hairs, and the position of the axis of the guiding sleeve is displayed as moving with respect to the cross-hairs. Other methods of displaying the position of the actual trajectory of the axis of the guiding sleeve with respect to the planned trajectory may also be used.

It is contemplated that the handheld computer and monitor unit may be adapted for use with any of the trajectory guides disclosed herein, either with or without a docking and quick-release interface. A benefit of including the docking and quick-release interface is that the handheld computer and monitor unit pivots with the guiding sleeve and maintains the display in a fixed alignment therewith. If the monitor device has a built in inertial sensor, then it is not necessary to have an added angle sensor device 812. A benefit of docking the unit with the guiding sleeve is the ability to use a display unit that has a built in level sensor that moves with the trajectory guide and guiding sleeve and is adapted to sense the first and the second angle of the axial guide member or guiding sleeve. The arrangement enables the display to present targeting information to the operator without the use of an external data connection.

Figure 11:
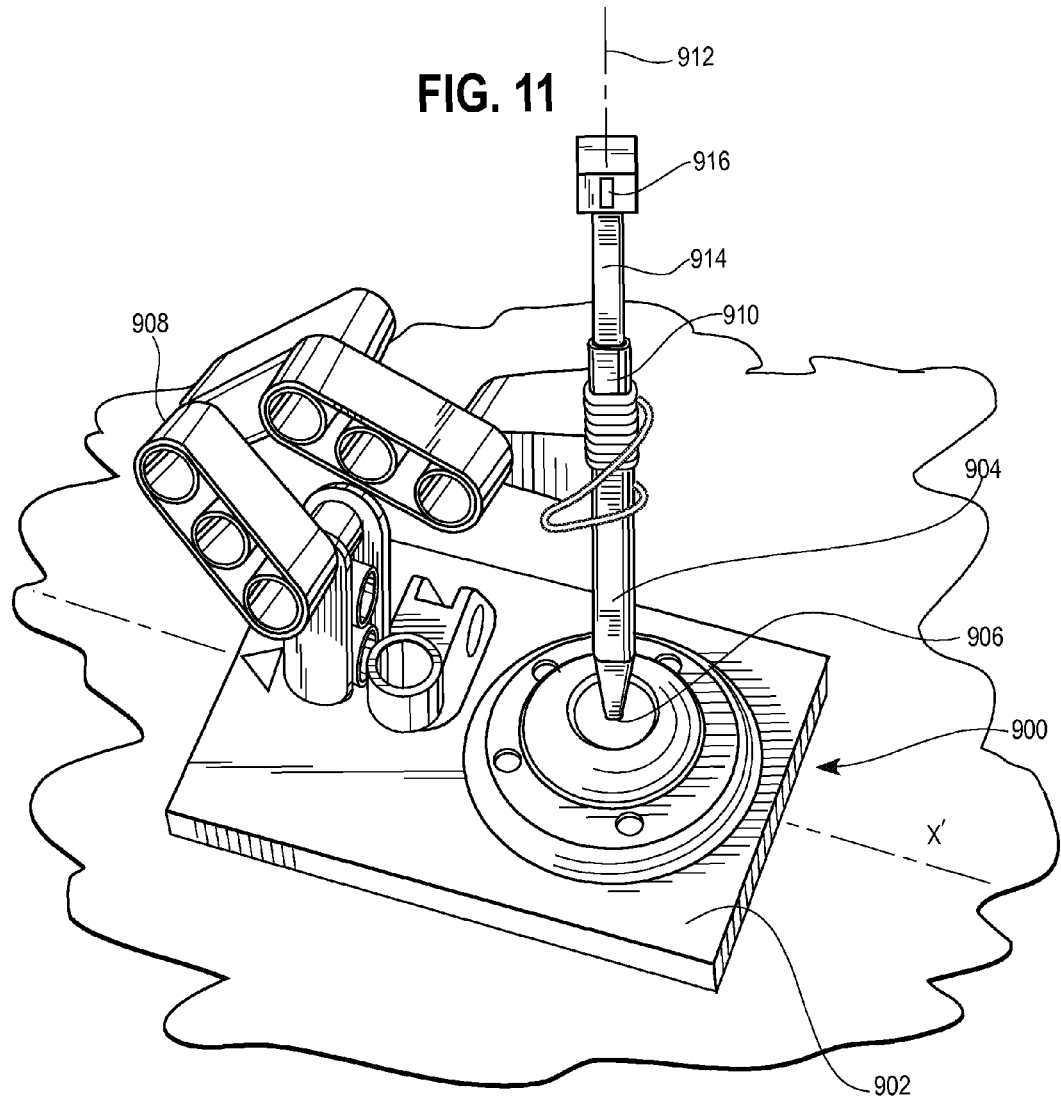
FIG. 11 is an isometric view of a further embodiment of the trajectory guide where the sensors are located on the instrument that is inserted into the guide.

FIG. 11 shows a further embodiment of the guide 500 shown in FIG. 6. A trajectory guide 900 has a base 902 and guiding sleeve 904. As in FIG. 6, the guiding sleeve 904 is attached to base 902 with a ball-and-socket connection 906 and as in FIG. 6 the guiding sleeve 104 is prevented from rotation about longitudinal axis 912 by a linking mechanism 908 attached to a distal end 910 of the guiding sleeve 904. The mechanics of the linking mechanism 908 are the same as in FIG. 6. One difference between FIGS. 6 and 11 is the cross-sectional shape of the guiding sleeve 904. Guiding sleeve 904 has an asymmetrical cross section that matches to cross section of needle 914. For instance, the cross sections of the guiding sleeve 904 and needle 914 could be any asymmetrical geometric shape, such as oval, elliptical, triangular, pentagonal, and the like. The particular shape is not important but the shape must be able to prevent needle 914 from rotating about the longitudinal axis 912. Needle 914 has one or more angle sensors 916 mounted thereon. The angle sensors 916 are mounted so that they are in a fixed and known relation to the X'-axis when the trajectory guide 900 is orientated with the X-axis of the CT gantry 104 using marker 918. Because there are angle sensors 916 mounted on the needle 914, it is not necessary to have an angle sensor mounted on the guiding sleeve 904. The trajectory guide 900 with the needle 914 inserted in the guiding sleeve 904 will operate in a manner similar to the previously described trajectory guides that have sensors mounted directly on the guide sleeve.

The main function of the various mechanical arrangements shown in the trajectory guides of FIGS. 2 and 5-11 is to limit and guide the alignment movements of the guiding sleeve with respect to the base such that the movements can be measured without interference, the pitch and yaw angles can be measured without needing to register or calibrate the angle sensors, and the alignment of the guiding sleeve can be adjusted in a controlled manner. Other aspects of the variations shown in FIGS. 2 and 5-11 are substantially functionally similar as described with reference to the schematic depiction of a generic trajectory guide of FIG. 2 and are incorporated as appropriate in the descriptions thereof.

There are many advantages and useful qualities of the trajectory guides described herein. For example, the trajectory guides work well in combination with the CT scanner if the coordinate systems of both devices are aligned with each other as described previously.

The trajectory guides make it possible to measure the pitch and yaw angles independently from each other. In detail this means that the two angles "pitch" and "yaw" can be set and measured independently from each other, and there is no other way to adjust the trajectory differently, i.e., modifying pitch and yaw are the only and explicit way to alter the trajectory's direction. Furthermore this means that a certain pitch and a certain yaw define a certain trajectory direction unambiguously. This can be explained most intuitively with reference to the two arc solution of FIG. 2. First the trajectory guide mechanics are aligned with the CT gantry such that the X-axes coincide (e.g. the "roll" angle is fixedly set to "zero"). Then the two arcs move in the directions of yaw (outer, larger arc) and pitch (inner, smaller arc) or vice versa. The two arcs move independently from each other and their angle values define the trajectory's direction unambiguously. Such single angular positions can be easily measured with separate angular sensors at each arc.

However, there are more sophisticated sensors, such as MEMS-based angle sensors, that are capable to measure several angular positions and movements into several well distinguished directions. For example, by attaching an angle sensor in an appropriate way to the trajectory guide, all required angle positions can be measured with that single angle sensor without requiting any levelling or calibration. In order to accomplish this, it is necessary again that the coordinate axes from the angle sensor are aligned with the desired movement directions that are to be measured, and any other movements into other directions that cannot be detected by the angle sensor must be prohibited. Examples of this are the solutions with a single arc and a rail shown in FIG. 5 and the rectangular translation guides shown in FIG. 8. In FIG. 5 with the single arc the mechanics of the single arc allows rotations only that are into the directions of the laser lines that indicate the directions of the X and Z coordinate axes of the imaging device.

As mentioned before, in some embodiments, it important to prohibit movement of the guiding sleeve when secured to the patient in degrees of freedom that cannot be measured by the sensors. Thus, it can be seen that in all of the described solutions, rotation around the Y-axis, i.e., by rotation about the longitudinal axis of the guiding sleeve, is prohibited. In other words, by prohibiting rotation in the "roll" direction and maintaining the alignment of the Z-axes of all involved components, it is possible for pitch and yaw to become absolute measures that define the trajectory unambiguously.

INDUSTRIAL APPLICABILITY

The axial surgical trajectory guides of the present invention are useful for setting a trajectory of a needle for obtaining a biopsy based on CT images and other surgical procedures that require guidance of an axial surgical instrument where the position of the patient relative to the local gravity vector is known or calculated. The axial surgical trajectory guides of the present invention can overcome the need for a separate surgical navigation system, such as an optical or magnetic system, that would require registration of the CT image with the data from the navigation system. Further, the axial surgical trajectory guides of the present invention eliminate the need to maintain the guide in a pre-defined relationship with respect to the horizontal plane or gravity vector. Thus, the axial surgical trajectory guides of the present invention provide a significant benefit by reducing the complexity of equipment necessary in the procedure or operating room and/or simplifying the actual procedure of aligning the guide by the operator while defining the selected trajectory in relation to the patient.

Although the trajectory guides herein are described with reference to use with CT scanners, it is clear that the trajectory guides may be used with other systems in which a coordinate system of a three-dimensional image of a patient can be physically transferred directly to the coordinate system of the trajectory guides by, for example, laser lines or other visible means, consistent with the principles disclosed herein.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved. All patents, patent applications, and other printed publications identified in this foregoing are incorporated by reference in their entireties herein.

We claim:

1. A surgical trajectory guide to guide a medical device to a pivot point comprising:
   a base, the base being attachable to a patient in a fixed position;
   an axial guide member pivotably connected with the base by a linkage,
      wherein the axial guide member is aligned with the pivot point along a first axis in fixed relation to the base and a second axis perpendicular to the first axis,
      wherein the axial guide member has a longitudinal axis,
      wherein the linkage allows pivoting movement of the axial guide member in a pitch direction and a yaw direction such that the longitudinal axis always passes through the pivot point, and
      wherein the linkage does not allow the axial guide member to rotate around the longitudinal axis relative to the pivot point during adjustments of the axial guide member in the pitch direction and in the yaw direction; and at least one electronic angle sensor associated with the axial guide member and adapted to automatically sense a first angle of the axial guide member relative to a local gravity vector about the first axis and a second angle of the axial guide member relative to the local gravity vector about the second axis without having to level the base.

2. The surgical trajectory guide of claim 1, further comprising a data connection adapted to allow transfer of the sensed first and second angles to an external system.

3. The surgical trajectory guide of claim 1, wherein the at least one electronic angle sensor is selected from an inertial sensor or a level sensor.

4. The surgical trajectory guide of claim 1, wherein the axial guide member comprises a hollow tubular member defining an axis extending through the pivot point.

5. The surgical trajectory guide of claim 1, further comprising a display unit that is rigidly connected with the axial guide member and moves therewith.

6. The surgical trajectory guide of claim 5, wherein the display unit comprises an integrated sensor adapted to sense the first and the second angle of the axial guide member.

7. The surgical trajectory guide of claim 2, wherein the transfer takes place between the at least one electronic angle sensor and a display unit, wherein the display unit is configured to display the current angle positions of the surgical trajectory guide with respect to a coordinate system of an imaging system.

8. The surgical trajectory guide of claim 1, further comprising an adhesive disposed on the base for attaching the base to the patient.

9. The surgical trajectory guide of claim 1, further comprising a marker associated with the base and disposed in a fixed position relative to the base, wherein the marker visually defines the first axis.

10. The surgical trajectory guide of claim 1, wherein the linkage comprises a first arcuate member attached to the base aligned with the first axis, wherein the first arcuate member is adapted to move about the first axis and the axial guide member is adapted to move along the first arcuate member about the second axis.

11. The surgical trajectory guide of claim 1, wherein the axial guide member is connected to the base with a ball-and-socket connection at the pivot point and the linkage does not allow the axial guide member to rotate about the longitudinal axis through the pivot point.

12. The surgical trajectory guide of claim 1, wherein the linkage limits movement of the axial guide member such that the axial guide member can only move about the pivot point in one degree of freedom that is in a plane of the first axis.

13. A method of guiding an axial medical instrument during a procedure comprising the steps of:

placing a trajectory guide having an axial guide member, which is pivotably connected to a base by a linkage, on a patient so that a predefined first axis of the base is aligned with a predetermined axis of an imaging device, wherein the axial guide member has a longitudinal axis that passes through a pivot point on the first axis, and wherein the linkage allows pivoting movement of the axial guide member in a pitch direction and a yaw direction, and the linkage does not allow the axial guide member to rotate around the longitudinal axis of the axial guide member relative to the pivot point during adjustments of the axial guide member in the pitch direction and the yaw direction;

adjusting the axial guide member so that the longitudinal axis is located on a planned trajectory for the axial medical instrument; and placing the axial medical instrument in the axial guide member to perform the medical procedure.

14. The method of claim 13 wherein the linkage is adapted to be adjusted to allow movement of the axial guide member about the pivot point in two independent degrees of freedom related to the first axis and a second axis.

15. The method of claim 13 wherein the linkage is adapted to be adjusted to allow movement of the axial guide member about the pivot point in only one degree of freedom that is in a plane of the first axis.

16. The surgical trajectory guide of claim 1, wherein the linkage further comprises a locking mechanism, the locking mechanism being configured to lock the axial guide member in a selected orientation relative to the base.

17. The surgical trajectory guide of claim 1, further comprising:
a carriage member that is fixedly secured to the axial guide member, wherein the carriage member is configured to slide along the first axis.

18. The surgical trajectory guide of claim 1, wherein the linkage comprises a pair of arcuate guides having a pair of slots, and a carriage member movably mounted in the pair of slots, wherein the axial guide member is attached to the carriage member.

19. The surgical trajectory guide of claim 1, wherein the linkage further comprises:
a first set of rails;
a second set of rails perpendicular to the first set of rails;
a first carriage member mounted to the first set of rails; and
a second carriage member mounted to the second set of rails;
wherein the axial guide member slides between slots in the first and second carriages.

20. The surgical trajectory guide of claim 1, wherein the linkage is attached to the base with a hinge joint.

* * * * *